United States Patent [19]

Pommer et al.

[11] 4,066,775

[45] Jan. 3, 1978

[54] CERTAIN FUNGITOXIC 2-HALO-5-TRICHLOROMETHYL-1,3,4-THIADIAZOLES

[75] Inventors: Ernst-Heinrich Pommer, Limburgerhof; Helmut Hagen, Frankenthal; Helmut Fleig, Mannheim, all of Germany

[73] Assignee: BASF Aktiengesellschaft, Rheinland-Pfalz, Germany

[21] Appl. No.: 688,761

[22] Filed: May 21, 1976

[30] Foreign Application Priority Data

June 12, 1975 Germany ............................ 2526308

[51] Int. Cl.$^2$ .................. A61K 31/425; C07D 285/12
[52] U.S. Cl. ............................ 424/270; 204/158 HA; 260/302 D
[58] Field of Search .................... 260/302 D; 424/270

[56] References Cited

U.S. PATENT DOCUMENTS 3,979,403   9/1976   Pivawer et al. ................ 260/302 D

OTHER PUBLICATIONS

Dunn et al., *Chem. Abstracts,* vol. 77, 3817CS and 1401098 ('72).
Lalezari et al., *J. Pharm. Sci.,* 1975, 64(7), 1250–1252.
Modarai et al., *J. Heterocyclic Chem.,* 1974, 11(3), 343–345.

*Primary Examiner*—Richard J. Gallagher
*Attorney, Agent, or Firm*—Keil, Thompson & Shurtleff

[57] ABSTRACT

This invention relates to new and valuable 2-halo-5-trichloromethyl-1,3,4-thiadiazoles having a good fungicidal action, fungicides containing these compounds as active ingredients, a method of controlling fungi with these compounds, and a process for their manufacture.

4 Claims, No Drawings

CERTAIN FUNGITOXIC 2-HALO-5-TRICHLOROMETHYL-1,3,4-THIADIAZOLES

It is known to use tetramethylthiuram disulfide (Chemical Week, July 26, 1972, p. 39), 5,6-dihydro-2-methyl-1,4-oxathiin-3-carboxanilide (Chemical Week, July 26, 1972, p. 41) and 5-ethoxy-3-trichloromethyl-1,2,4-thiadiazole (Chemical Week, July 26, 1972, p. 38) as fungicides. However, their action is poor.

It was therefore the object of the present invention to develop new active ingredients and fungicides having a better fungicidal action.

We have now found that 2-halo-5-trichloromethyl-1,3,4-thiadiazoles of the formula

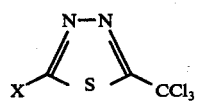

II, where X denotes chloro or bromo, have a better fungicidal action than the abovementioned prior art compounds. The new ingredients are particularly effective on molds, e.g., *Aspergillus niger*, and on Basidiomycetes, e.g., *Rhizoctonia solani* and *Coniophora cerebella*. The active ingredients may be used to protect not only plants but also wood and other materials. The active ingredients may be mixed with other prior art fungicides, this often increasing the fungicidal spectrum. When the compounds are used as plant protection agents, the application rates vary, depending on the effect desired, from 0.2 to 5 and more, preferably from 0.5 to 2, kg of active ingredient per hectare. When they are used as fungicides for protecting wood and other materials, 0.05 to 2% (by weight) solutions or dispersions of the active ingredients are employed for coating, spraying, dipping and impregnating.

The new compounds are obtained by reacting 2-trichloromethyl-1,3,4-thiadiazole

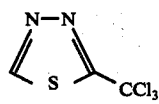

with chlorine or bromine at elevated temperature and under the action of radiation.

Nuclear halogenations of 1,3,4- and 1,2,4-thiadiazoles are not known. Whereas homocyclic aromatic compounds are usually nuclear-chlorinated with Lewis catalysts in the cold, 2-trichloromethyl-1,3,4-thiadiazole gives either no reaction product under analogous reaction conditions, or, at elevated temperature, large amounts of decomposition products; it was therefore surprising how smoothly the halogenation of this compound proceeds in the melt at elevated temperature and with or without radiation, and at any rate without catalyst.

The 2-trichloromethyl-1,3,4-thiadiazole used as starting product may be prepared by reacting 2,5-bis-trichloromethyl-1,3,4-thiadiazole (German Laid-Open Application DOS 2,253,863) with concentrated sulfuric acid at elevated temperature. The following specification illustrates this process.

Manufacturing specification for 2-trichloromethyl-1,3,4-thiadiazole 6.4 parts by weight of 2,5-bis-trichloromethyl-1,3,4-thiadiazole is heated in 30 parts by volume of 91% sulfuric acid for 6 minutes at 175° to 185° C. The reaction mixture is subsequently poured carefully on to ice and the precipitated solid is filtered off. The reaction product is washed with water and treated with 20 parts by volume of methanol, and the minor amounts of undissolved starting material are filtered off. Concentration of the methanolic solution gives 3.4 parts (83% of theory) of 2-trichloromethyl-1,3,4-thiadiazole having a melting point of 58° C.

The reaction for producing the new 2halo-5-chloromethyl-1,3,4-thiadiazoles is generally carried out at from 60° to 180° C, preferably from 120° to 160° C in the case of chlorination and preferably from 90° to 130° C in the case of bromination, without solvent, at atmospheric, subatmospheric or superatmospheric pressure, and continuously or batchwise. Per mole of starting material (compound II) there are used from 1 to 1.5 moles, preferably from 1.01 to 1.2 moles, of halogen. The halogen is fed in at a rate of from 0.1 to 2 moles, preferably from 0.2 to 0.6 mole, per hour.

Chlorination may be carried out as follows. 1.1 times the stoichiometric amount of chlorine is passed at a rate of from 0.4 to 0.5 mole per hour into a melt of compound II which is at 140° to 150° C and irradiated with an ultraviolet lamp. The reaction mixture is then distilled. Bromination is carried out analogously by dripping in bromine at 110° to 130° C.

The fungicidal action of 2-chloro-5-trichloromethyl-1,3,4-thiadiazole, one of the compounds of the invention, is very good; it also has a weak herbicidal action on dicotyledons and injures saprophytic soil nematodes.

2-bromo-5-trichloromethyl-1,3,4-thiadiazole also has an excellent fungicidal action.

The preparation of the new compounds is described in more detail in the following examples.

EXAMPLE 1

Over a period of 2 hours, about 15 liters of chlorine is passed into a melt of 102 g of compound II at 140° to 150° C and which is irradiated with an ultraviolet lamp (100 watts). The reaction mixture is then distilled. At 83° to 85° C (1 mm Hg) there is obtained 108 g (91% of theory) of 2-chloro-5-trichloromethyl-1,3,4-thiadiazole having a melting point of 41° C.

EXAMPLE 2

Over a period of 1 hour and at 120° to 130° C, 89 g of bromine is dripped into a melt of 102 g of compound II subjected to ultraviolet irradiation (50 watts). The reaction mixture is then distilled. At 102° to 104° C (1 mm Hg) there is obtained 82 g (58% of theory) of 2-bromo-5-trichloromethyl-1,3,4-thiadiazole having a melting point of 39° C.

Application may be effected for instance in the form or directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, furher coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives for formaldehyde, condensation products of napthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, oxide, ground plastics, fertilizers such as ammonium sulfate, ammonium phosphate, ammonium nitrate, and ureas, and vegetable products such as grain flours, bark meal, wood meal, and nutshell meal, cellulosic powders etc.

The formulations contain from 0.1 to 95, and preferably 0.5 to 90%, by weight of active ingredient.

EXAMPLE 3

The active ingredients are added to a nutrient solution ideally suited for promoting the growth of the fungus *Aspergillus niger* in amounts of 100, 50, 25, 10 and 5 parts by weight per million parts of nutrient solution. 20 ml of the solution treated in this manner is placed in 100 ml glass flasks and inoculated with 0.3 mg of Aspergillus spores. The flasks are heated for 120 hours of 36° C. The extent of fungus spread — predominantly on the surface of the nutrient solution — is then assessed.

0 = no fungus growth, graded down to 5 = uncontrolled fungus growth (surface of nutrient solution completely covered by fungus)

| Active ingredient | Amount of active ingredient in nutrient solution in ppm of solution | | | | |
|---|---|---|---|---|---|
| | 100 | 50 | 25 | 10 | 5 |
| N—N ‖   ‖ Cl⌒S⌒CCl₃ | 0 | 0 | 0 | 0 | 2 |
| N—N ‖   ‖ Br⌒S⌒CCl₃ | 0 | 0 | 0 | 0 | 0 |
| Tetramethylthiuram disulfide | 1 | 2 | 4 | 5 | 5 |
| Control (untreated) | | | 4 | | |

EXAMPLE 4

Cotton seeds of the Delta Pine variety are thoroughly dusted with a seed disinfectant preparation containing, in ground form, 40% (wt%) of the active ingredient under investigation and 60% of talc, in an amount of 0.3 g per 100 g of seed. The cotton seeds treated in this manner are placed in pots and covered with soil which has previously been artifically inoculated with the fungus *Rhizoctonia solani*. After 21 days the extent of the disease is assessed; a prior art fungicide and an untreated control are used for comparison purposes.

| Active ingredient | Diseased cotton plants in % (21 days after emergence) |
|---|---|
| N—N ‖   ‖ Cl⌒S⌒CCl₃ | 1 |
| N—N ‖   ‖ Br⌒S⌒CCl₃ | 6 |
| H₂⌒O⌒CH₃ H₂⌒S⌒CO—NH—Ph prior art | 11 |
| Control (untreated) | 85 |

EXAMPLE 5

The active ingredients are dissolved in acetone in amounts of from 0.01 to 0.005% (by weight) and uniformly distributed in a still liquid nutrient malt agar. The agar is then poured into glass dishes having a diameter of 9 cm. After the agar has solidified, the dishes are centrally inoculated with mycelium flakes of the fungi *Fusarium nivale, Rhizoctonia solani* and *Coniphora cerebella*. The dishes were incubated at 25° C and after 6 days the spread of the fungus colony is assessed in accordance with the following scale:

| | |
|---|---|
| 0 = no fungus growth | |
| 1 = diameter of fungus colony | 0.5 to 1.5 cm |
| 2 = diameter of fungus colony | 1.5 to 3.5 cm |
| 3 = diameter of fungus colony | 3.5 to 4.5 cm |
| 4 = diameter of fungus colony | 4.5 to 7 cm |
| 5 = diameter of fungus colony | 7 to 9 cm |

| Active ingredient | Active ingredient in agar in % | Fusarium nivale | Rhizoctonia solani | Coniphora cerebella |
| --- | --- | --- | --- | --- |
| N—N, Cl–S–CCl₃ | 0.01 | 0 | 0 | 0 |
| | 0.005 | 0 | 0 | 0 |
| | 0.0025 | 2 | 0 | 0 |
| | 0.001 | 3 | 1 | 0 |
| | 0.0005 | 4 | 4 | 0 |
| N—N, Br–S–CCl₃ | 0.01 | 0 | 0 | 0 |
| | 0.005 | 1 | 0 | 0 |
| | 0.0025 | 2 | 0 | 0 |
| | 0.001 | 4 | 3 | 0 |
| | 0.0005 | 5 | 5 | 3 |
| Cl₃C–N=N–S–OC₂H₅ | 0.01 | 2 | 1 | 3 |
| | 0.005 | 4 | 2 | 4 |
| | 0.0025 | 4 | 3 | 4 |
| | 0.001 | 4 | 4 | 5 |
| | 0.0005 | 5 | 5 | 5 |
| prior art | | | | |
| Control (untreated) | — | 5 | 5 | 5 |

EXAMPLE 6

90 parts by weight of the compound of Example 1 is mixed with 10 parts by weight of N-methyl-α-pyrrolidone. A mixture is obtained which is suitable for application in the form of very fine drops.

EXAMPLE 7

20 parts by weight of the compound of Example 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 10,000 parts by weight of water and uniformly distributing it therein, an aqueous dispersion is obtained containing 0.2% by weight of the active ingredient.

EXAMPLE 8

20 parts by weight of the compound of Example 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 10,000 parts by weight of water and uniformly distributing it therein, an aqueous dispersion is obtained containing 0.2% by weight of the active ingredient.

EXAMPLE 9

20 parts by weight of the compound of Example 2 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 10,000 parts by weight of water and uniformly distributing it therein, an aqueous dispersion is obtained containing 0.2% by weight of the active ingredient.

EXAMPLE 10

20 parts by weight of the compound of Example 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silic gel, and triturated in a hammer mill. By uniformly distributing the mixture in 20,000 parts by weight of water, a spray liquid is obtained containing 0.1% by weight of the active ingredient.

EXAMPLE 11

3 parts by weight of the compound of Example 1 is intimately mixed with 97 parts by weight of particulate kaolin. A dust is obtained containing 3% by weight of the active ingredient.

EXAMPLE 12

30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. A 2-halo-5-trichloromethyl-1,3,4-thiadiazole of the formula

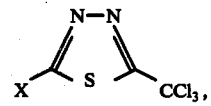

where X denotes Cl or Br.
2. 2-chloro-5-trichloromethyl-1,3,4-thiadiazole.
3. 2-bromo-5-trichloromethyl-1,3,4-thiadiazole.
4. A process for combatting fungi wherein the objects to be protected against fungus attack, or the fungi themselves, are treated with a fungitoxic amount of a 2-halo-5-trichloromethyl-1,3,4-thiadiazole of the formula

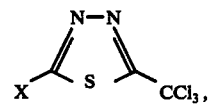

where X denotes Cl or Br.